United States Patent [19]

Ellis et al.

[11] Patent Number: 4,702,246
[45] Date of Patent: Oct. 27, 1987

[54] HEATING INSTRUMENT FOR TREATING A DEFORMED NAIL

[75] Inventors: Cedric R. Ellis, 16 Grosvenor Rd., Scarborough, Yorkshire, England, YO11 2NA; Peter G. Long, Upper Poppleton, England; Christopher A. Marshman, Dunnington, England; David J. Gillery, Acomb, England

[73] Assignee: Cedric R. Ellis, Yorkshire, England

[21] Appl. No.: 758,400

[22] Filed: Jul. 24, 1985

[30] Foreign Application Priority Data

Jul. 24, 1984 [GB] United Kingdom ............... 8418796

[51] Int. Cl.⁴ ............................................. A61B 17/00
[52] U.S. Cl. ................................................. 128/303.1
[58] Field of Search ........... 128/303.1, 303.12, 303.17, 128/321-326, 354, 399, 303 R

[56] References Cited

U.S. PATENT DOCUMENTS

| | | | |
|---|---|---|---|
| 702,472 | 6/1902 | Pignolet | 128/303.1 |
| 728,883 | 5/1903 | Downes | 128/303.1 |
| 1,083,386 | 1/1914 | Chapman | 128/303.1 |
| 1,234,570 | 7/1917 | Rink | 128/303.1 |
| 2,777,445 | 1/1957 | Hart | 128/303.12 |
| 2,779,854 | 1/1957 | Hebing | 128/303.1 |
| 3,742,187 | 6/1973 | Folus | 128/303.1 |
| 3,826,263 | 7/1974 | Cage et al. | 128/303.1 |
| 3,840,016 | 10/1974 | Lindemann | 128/303.17 |
| 3,938,526 | 2/1976 | Anderson et al. | 128/303.1 |
| 3,980,861 | 9/1976 | Fukunager | 128/303.1 |
| 4,046,148 | 9/1977 | Meador | 128/303.1 |
| 4,213,460 | 7/1980 | Weiner | 128/303 R |
| 4,449,528 | 5/1984 | Auth et al. | 128/303.1 |

FOREIGN PATENT DOCUMENTS

| | | |
|---|---|---|
| WO83/02389 | 7/1983 | PCT Int'l Appl. |
| 8814 | of 1914 | United Kingdom |
| 2040689 | 9/1980 | United Kingdom |

OTHER PUBLICATIONS

"Thermal Correction of Involuted Nails", The Chropodist, 1970, Back.

Primary Examiner—William E. Kamm
Assistant Examiner—Max F. Hindenberg
Attorney, Agent, or Firm—Murray and Whisenhunt

[57] ABSTRACT

Pliers are disclosed for the treatment of ingrowing nails on the human body. The pliers comprise first and second jaws. The upper jaw has a support member on which there is mounted an electrical heating wire. A slot in the lower jaw is adapted to receive the support member and wire.

In use, the pliers grip are ingrowing toe nail, and an electric heating current is applied to the wire, to cause local heating of the nail. The nail thus softens, and can be bent back into better shape, which shape is retained upon subsequent cooling of the nail. The lower jaw is of a relatively great heat mass, so as to ensure that no undue heating of the nail plate occurs. Control circuitry is provided for controlling the heating current through the heating wire, optionally in dependence upon a detected temperature.

15 Claims, 10 Drawing Figures

HEATING INSTRUMENT FOR TREATING A DEFORMED NAIL

This invention relates to instruments for use in treating horny structures on animal bodies and is concerned particularly although not exclusively with the treatment of ingrowing nails on the human body.

At the present time, ingrowing toe nails are often treated by removal of part of the nail, following which some mechnical means is employed in an attempt to cause the nail to grow in a more normal position. Such mechanical means may include nail braces, and very often, some sort of packing placed between the nail and the nail bed. In certain cases, an ingrowing toe nail may be removed completely.

Such known methods meet with varying degrees of success. However, their main area of success is in relieving pain. They are not always successful in effecting a cure to the condition, which often recurs.

It has been appreciated that nails are horny structures, and horn is a natural thermoplastic. Thus, if it were possible to apply heat to an ingrowing toe nail, it may be possible to bend the nail away from its deformed position, towards a more normal position. However, the problem arises then of how to apply heat to a nail in a controlled manner. Sufficient heat must be applied to enable the nail to become soft. On the other hand, care must be taken not to overheat the surrounding area, which would tend to cause even more pain to the patient.

In "The Chiropodist" of 1970, pages 391 and 394, there is an article by Arthur C. Back, M.Ch.S.,S.R.Ch., entitled "Thermal Correction Of Involuted Nails". In this article, the author discloses and describee a pair of forceps, which are adapted to be used to apply heat to a severely involuted nail, such that it may be bent into a better shape. The forceps comprise metal bodies of substantial heat mass, which are adapted to be raised to 100° C. and then applied to the nail. Although the author found that the application of heat was beneficial, the apparatus described has a number of disadvantages. Firstly, the entire mass of the forceps is raised to 100° C., so that there is a real risk of discomfort to the patient, due to any contact of the lower forceps body with the nail plate. Secondly, the very basic design of the forceps does not facilitate dexterous operation—especially also as the forceps themselves are at 100° C. Thirdly, the temperature of the forceps is raised by immersion in boiling water, thereby limiting the maximum temperature to 100° C. The author of the article states this to be an advantage, in so far as risk of damage by over heating is minimised. However, this is only an advantage in so far as it mitigates a disadvantage of the basic design of the forceps in the first place—namely, that the hot forceps body is likely to cause unwanted contact with the patient's body. In fact, we have discovered that a temperature greater than 100° C. is desirable, provided that this is confined to the appropriate area.

Preferred embodiments of the present invention aim to provide instruments which may be used in the treatment of nails, and which may be generally improved in the foregoing respects.

According to a first aspect of the present invention there is provided an instrument for use in treating a horny structure on an animal body, the instrument comprising first and second jaws adapted to grip part of a horny structure therebetween and means for closing and opening the jaws, wherein electrical heating means is arranged to heat at least a portion of the first jaw, and control means is arranged to control the heating current through the electrical heating means.

The instrument is preferably adapted to treat nails.

The instrument is preferably in the form of a pair of pliers or forceps. Surgical pliers and forceps are manufactured in many different forms, some of them especially for the treatment of ingrowing toe nails, and any such suitable forms may be employed in pliers or forceps embodying with the present invention. In particular, the pliers or forceps may be provided with releasable locking means for locking the jaws in a closed position.

The instrument preferably comprises a body which is at least principally formed of an electrically conductive material, from which the electrical heating means is electrically insulated. Then, the electrical supply to the electrical heating means may incorporate an electrical path through said body.

The electrical heating means may comprise an electrical resistance wire mounted on an electrically insulative support. The arrangement may be such that, in use, the electrical resistance wire is arranged to contact a horny structure directly.

The control means may be operative to limit said current to a predetermined value, and may include means for adjusting that predetermined value.

The control means may include temperature sensor means arranged to sense temperature in the vicinity of said first jaw portion, said control means being arranged to control said current in repsonse to an output of said sensor means.

Preferably, said control means includes a timer arranged to allow said current to flow for a predetermined time. The timer may include means for adjusting said predetermined time.

Where the timer is provided, the control means may be so arranged that in use, said current is caused to flow at a first, high level for a first predetermined time, and then at a second, lower level for a second predetermined time. Where a temperature sensor means is provided, the current may flow at a first, high level until a predetermined temperature is reached, whereafter the current is regulated to maintain the required temperature for a period determined by the timer.

The timer may include an indicator for indicating at least one point in an operating procedure of the control means. Said point may occur just before, when, or just after the control means switches off said current. The indicator may show when a current is flowing or when the timer is on.

In a preferred arrangement, at least one of said jaws has an area which is arranged to be disposed adjacent the body of an animal and is so arranged as to undergo no appreciable rise in temperature under any heating effect of said heating means. To this end, said one jaw may have a heat mass which is high relative to that of said first jaw portion. Additionally for alternatively, said one jaw may be thermally insulated from said first jaw portion.

According to a second aspect of the present invention, there is provided an instrument for use in treating a horny structure on an animal body, the instrument comprising first and second jaws adapted to grip part of a horny structure therebetween and means for closing and opening the jaws wherein electrical heating means is provided to heat at least a portion of the first jaws, and at least one of the jaws has an area which is arranged to be disposed adjacent the body of an animal and is so arranged as to undergo no appreciable rise in temperature under any heating effect of said heating means.

For a better understanding of the invention and to show how the same may be carried into effect, reference will now be made, by way of example, to the accompanying diagrammatic drawings, in which.

In the figures, like reference numerals denote like or corresponding parts.

Figure 1:
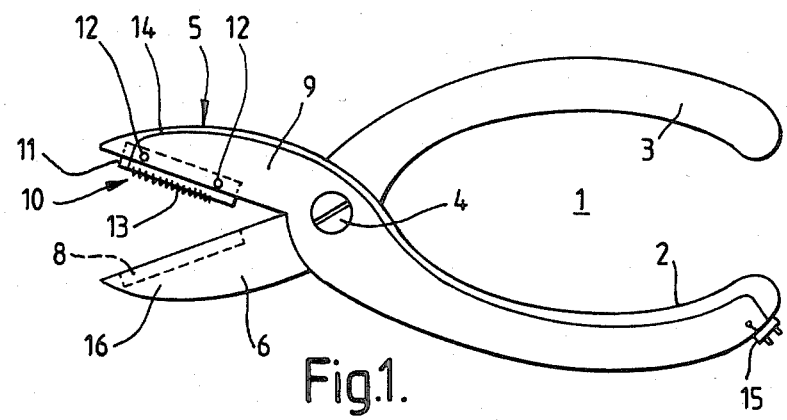
FIG. 1 is a side view of a pair of pliers for use in treating ingrowing toe nails.
Figure 2:
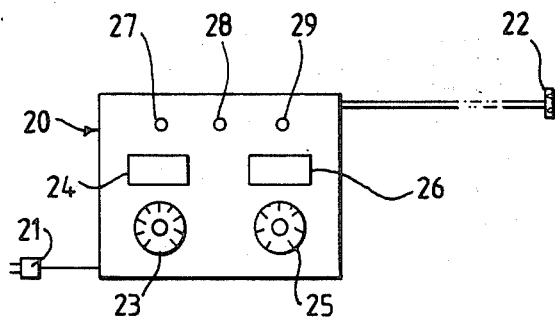
FIG. 2 illustrates control means for use with the pliers of FIG. 1.
Figure 3:
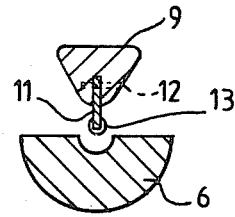
FIG. 3 is a cross-sectional view of the jaws arrangement of the pliers.

The pliers 1 which are shown in FIGS. 1 to 3 comprise a first handle 2 and a second handle 3, which are pivotally connected at 4. If desired, means (not shown) may be provided for locking the handles 2 and 3 together in a closed position of the pliers 1. A first jaw assembly 5 is provided at the front end of the first handle 2, and a second jaw 6 is provided at the front end of the second handle 3.

Figure 4:
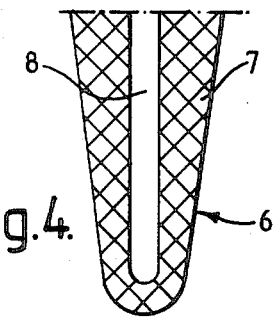
FIG. 4 is an enlarged plan view of a lower jaw of the pliers.

With reference to FIG. 4, the second, lower jaw 6 of the pliers 1 is of a fairly conventional shape, comprising a milled upper surface 7 which is adapted to grip underneath a nail, in use. In this example, the second jaw 6 is formed with an elongate slot 8 which opens into the upper surface 7.

The first, upper jaw assembly 5 comprises a jaw body 9 which, in a conventional pair of surgical pliers, would serve directly as a jaw, to co-operate with the lower jaw 6. However, in the illustrated pliers 1, the jaw body 9 serves as a mounting for an actual jaw member 10, which comprises a support member 11 of electrically insulative material, which is mounted in a groove provided therefor in the jaw body 9, and retained in that groove by means of a pair of mounting screws 12. An electrical resistance heating wire 13 is mounted on the support member 11. In this example, the wire is wound through holes provided in the support member 11. However, it is to be understood that an electrical heating element in any other suitable form may be employed.

The pliers 1 are made principally of metal, such that they readily conduct electricity. Thus, one end of the heating wire 13 is connected to one of the mounting screws 12, which is also of metal, to make electrical contact with the jaw body 9. The other end of the heating wire 13 is connected by a conductor 14 to one terminal of a two-pin plug connector 15, which is mounted at one end of the first handle 2. The other terminal of the plug connector 15 is electrically connected to the first handle 2, and thereby to the first-mentioned end of the heating wire 13.

FIG. 2 shows a controller 20 for use with the pliers 1. The controller 20 is adapted to receive mains voltage (e.g. at 240 volts) by way of a plug connector 21, and to derive therefrom a low voltage which is output on a socket connector 22, for connection with the plug connector 15 on the pliers 1. A first user control 23 is provided on the controller 20, for adjusting the value of the current which is output via the socket connector 22. A first display 24 displays the value of current output by the controller 20, or the setting of the control 23. A second user control 25 is provided, for adjusting the time for which an output current from the controller 20 flows. A second display 26 indicates the time setting of the control 25, the time elapsed since switch-on, or the time remaining until switch-off. Three indicators 27, 28 and 29 are provided on the controller 20, for indicating respective points in the operating cycle of the controller 20.

Operation of the instrument as illustrated in FIGS. 1 to 4 will now be described, by way of example, in which it will be assumed that an ingrowing toe nail of a patient's foot is to be treated.

Firstly, the foot and nail of the patient is examined in the usual way, and all aseptic precautions are taken. The operator then sets the controls 23 and 25 on the controller, to adjust respectively the level of heating current and time of operation. These parameters will vary in dependence upon the nature of the nail to be treated—e.g. its thickness, degree of deformity, etc. The lower jaw 6 of the pliers 1 is placed underneath the nail, and the upper jaw member 10 brought into contact with the upper surface of the nail. The nail is thus gripped between the co-operating jaw members 6 and 11. With the plug and socket connectors 15 and 22 joined together, the controller 20 is then switched on, such that a low voltage supply of heating current is fed to the heating wire 13.

The temperature of the upper jaw member 10 therefore rises, and as the nail becomes heated, it becomes softer and more pliable. After a first predetermined time, the first indicator 27 is lit, to indicate to the operator that the nail should be sufficiently heated to be capable of being bent. After a further, second predetermined time, the heating current is switched off by the controller 20, and the second indicator 28 is lit. After a further, third predetermined time, the third indicator 29 is lit. An audible alarm (e.g. a buzzer) may be operated each time any one of the indicators 27, 28 and 29 is lit.

Upon the first indicator 27 being lit, the operator begins to bend the ingrowing nail gently, to try to return it to a more normal position. The operator continues to do this, until the nail assumes its desired position. It will be appreciated that, when the heating current is switched off (as indicated by the indicator 28), the upper jaw member 10 and the nail begin to cool, and the nail begins to lose its pliability. The operator holds the nail in its desired position until it has cooled sufficiently to retain its new shape. The third indicator 29 is intended to indicate approximately when sufficient time has elapsed after turn off of the heating current, for the nail to be sufficiently cool as to retain its new shape.

It will be appreciated that it is of great importance to ensure that heat of the right quantity is applied to the right part of the nail, and that the patient is not subjected to discomfort by burning. In particular, the front lower area 16 of the lower jaw 6, which contacts the nail bed, should undergo no appreciable rise in temperature under any heating effect of the heating means. To this end, the jaw member 10 is preferably of a low heat mass, such that it may heat up and cool down relatively quickly. By contrast, the lower jaw 6 is of a relatively substantial heat mass. Being in contact with the underside of the nail, it readily absorbs any heat dissipated through the nail, and prevents the temperature underneath the nail from rising too high. It will therefore be appreciated that it is advantageous to place a heat sink under the nail. Indeed, in the illustrated arrangement, it may be possible to heat the jaw member 10 rapidly to a temperature of at least 100° C. (for example of around 120° C. or in the range 100° C. to 150° C.), to permit rapid bending of a nail with minimum discomfort to the patient, and without damage to the nail plate. It may be desired to raise the temperature locally to 150° C. or more, to achieve the desired degree of softening of the nail.

It will be appreciated that, once the temperature of the upper jaw member 10 has reached a safe operating level, then only a relatively low heating current may be required to maintain that temperature. However, if the heating current were always to be at that low level, then the initial rate of heating may be unacceptably low. Therefore, the controller may be arranged to control the current in a two stage cycle. Firstly, the heating current is caused to flow at a first, high level for a first predetermined time, during which the upper jaw member 10 heats up quite rapidly. There may be a pre-set device inside the controller, for adjusting the maximum current which the controller 20 may output, to ensure that dangerously high currents are always avoided. Then, after this first predetermined time, the current is caused to flow at a second, lower level, to maintain the jaw member 10 at approximately the desired temperature. In such an arrangement, the first user control 23 may be operative to adjust the first, high level of current, second, low level of current, or both. The second user control will be operative to control the overall time of flow of heating current but may also control also the first predetermined time for which the higher current flows.

Typically, the first indicator 27 may light at either a predetermined time after the heating current has commenced flow, or a predetermined time before the heating current is to be switched off. When the indicator 28 is lit, the operator knows that the nail will be beginning to cool. The third indicator 29 is typically arranged to be lit a predetermined time after the heating current has been switched off.

The controller 20 preferably comprises controllable semiconductor devices, by which the heating current is controlled in the desired manner. It is preferred that the controller is arranged to produce a low voltage output (e.g. 24 volts or less) at constant current, although the level of this constant current may be adjusted either under the first user control 23 or under the automatic two-cycle control mentioned above. For example, the output from the controller 20 may be of chopped d.c. form, the mark/space ratio of which may be varied to vary the current. However, if the controller 22 were adapted to provide a constant voltage output rather than a constant current output, then variable resistances may be provided in the current path, for adjusting the heating current to a desired value, in dependence upon the particular resistance of the heating wire 13.

It will be appreciated that the upper jaw assembly may take any suitable configuration. The configuration illustrated approximates to that of a prototype that I have built and tested, with satisfactory results. The heating wire 13 itself may be disposed in any suitable manner or configuration. It may be moulded into nylon or other material. The heating wire need not make direct contact itself with the nail. For example, it may heat a metallic jaw member which is, nevertheless, preferably of a relatively low heat mass.

The lower jaw 6 may also have any desired shape. In the illustrated example, the slot 8 may be specially useful where an attempt is made to bend upwardly an ingrowing toe nail. However, for other applications, the slot 8 may be omitted, such that the upper surface 7 of the lower jaw 6 is flat.

Figure 5:
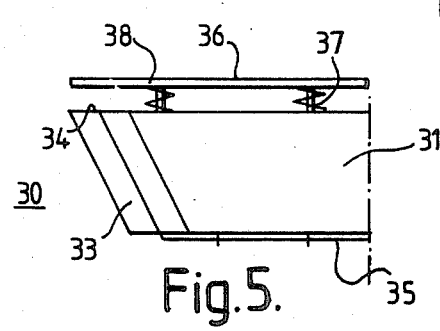
FIG. 5 is a longitudinal section of part of an instrument for use in treating involuted toe nails.
Figure 6:
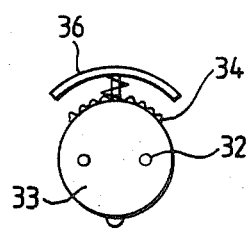
FIG. 6 is an end view of the instrument of FIG. 5.

The instrument 30 that is shown in FIGS. 5 and 6 operates on a similar principle to the instrument of FIGS. 1 to 4, but is specially adapted to treat involuted nails—i.e. those suffering from the condition which is also known as "excessive curvature".

The instrument 30 comprises a body 31 which is of metal or a heat resistant plastics material, and may have a length of the order of 10 to 15 cm. The body 31 is of circular cross-section, having a diameter of the order of 5 to 15 mm. At the front of the body 31 there is secured, by means of screws 32, a jaw body 33 of thermally and electrically insulative material. Mounted around the top arcuate surface of the jaw body 33 is an electrical resistance heating wire 34, to which electrical connections are made via conductors 35.

Mounted at the top of the body 31 is an arcuate metal plate 36. This is mounted on the body 31 by means of bolts 37, around each of which there is disposed a compression spring 38, which serves to urge the plate 36 away from the body 31.

In use, the upper arcuate portion of the jaw body 33 and the corresponding lower face of the metal plate 36 serve as first and second jaws which are adapted to grip part of a nail therebetween. Thus, in use, the jaw body 33 is inserted under an involuted nail, the forward part of which is clamped between the upper part of the jaw body 33 and the lower part of the plate 36.

The heating wire 34 is then subjected to a heating current by, for example, a controller 20 such as is shown in FIG. 2. This causes heat to be applied to the under side of the nail, which gradually becomes soft, until it may be bent towards a more normal shape. Thus, the instrument 30 is used in a similar manner to the pliers 1, except that it is more specificially adapted to the condition of involuted nails.

It will be appreciated that the plate 36 serves as a heat sink for excess heat from the nail being treated. In a variant, however, the heating wire 34 may be mounted on a thermally insulating plate, which in turn is fixed to the jaw body 33 which, in this case, is also of metal and is therefore operable as a heat sink. In this example, therefore, there would again be a heat sink placed under the nail.

The body 31 and/or the body 33 may alternatively be square, rectangular or oval in section.

Although both the pliers 1 and the instrument 30 are each provided with a heat sink on their respective second jaws, this may not be essential in all embodiments. For example, the second jaws may be made of thermally insulative materials.

Figure 7:
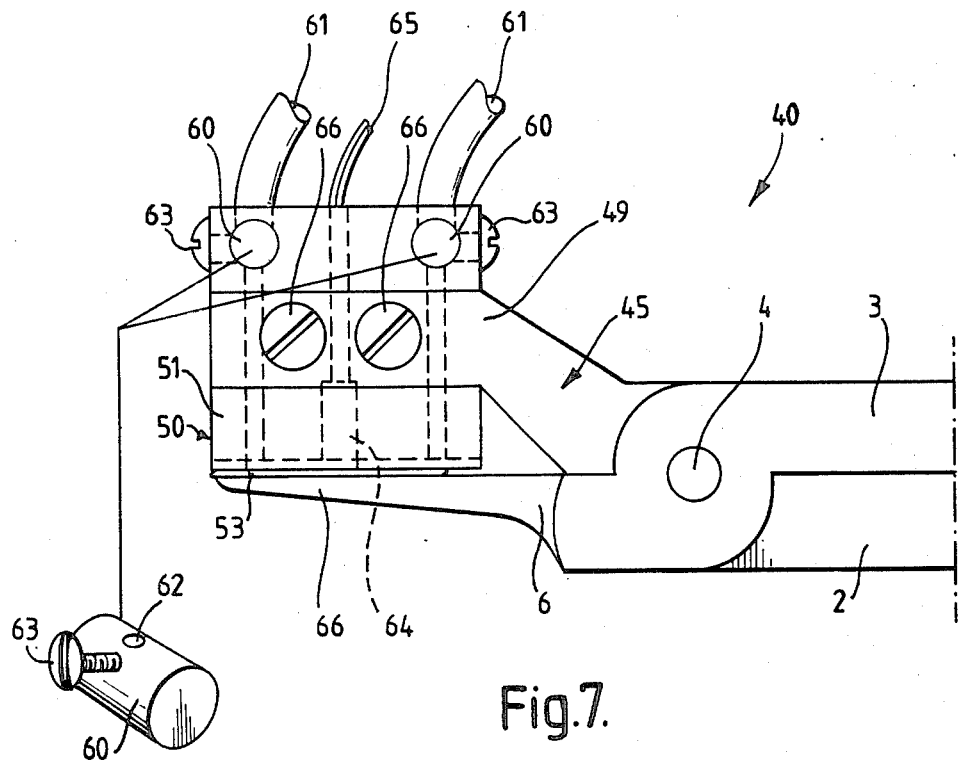
FIGS. 7 and 8 show part of an alternative pair of pliers, respectively in side and end elevation.
Figure 8:
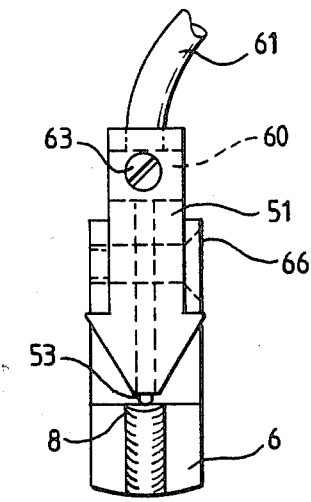

The pliers 40 that are shown in FIGS. 7 and 8 are similar in the basic essentials to the pliers 1 of FIG. 1, comprising first and second handles 2, 3, which are pivotally connected at 4, there being a first jaw assembly 45 provided at the front end of the first handle 2, and a second jaw 6 provided at the front end of the second handle 3. The second jaw 6 is formed with an elongate slot 8.

In FIGS. 7 and 8, however, the construction of the first jaw assembly 45 is somewhat different. The first jaw assembly 45 comprises a bifurcate jaw body 49, within which there is mounted a jaw member 50, comprising a support member 51 of electrically insulative material, on the lower edge of which there is disposed an electrical resistance heating wire 53. The opposite ends of the heating wire 53 are connected to respective terminal blocks 60, one of which is shown in an exploded perspective portion, in FIG. 7. Each terminal block 50 has an aperture 62 to receive a respective supply conductor 61, which is secured in position by means of a fastening screw 63.

The support member 51 is formed with a central bore, within which there is disposed a thermistor 64, which is connected to a pair of conductors 65, and which is disposed adjacent the heating wire 53.

The support member 51 is secured within the jaw body 49 by means of a pair of clamping screws 66.

Figure 9:
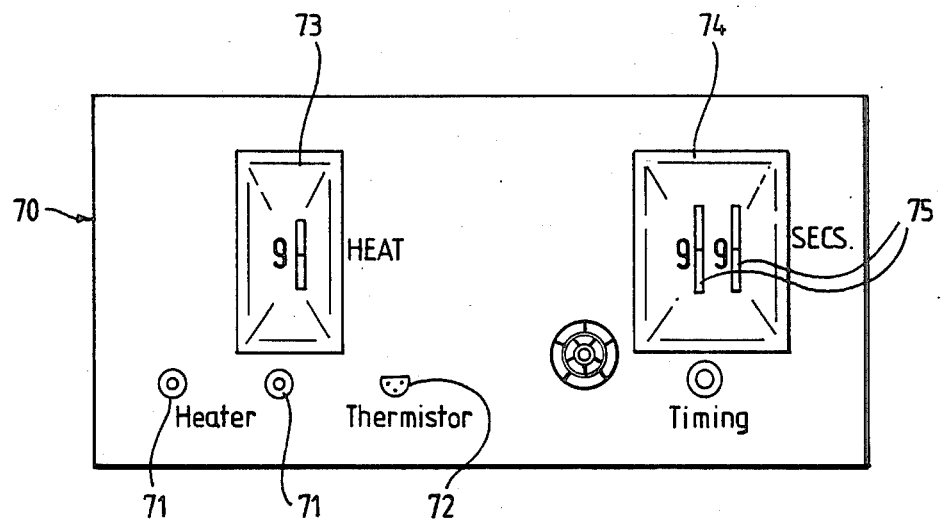
FIG. 9 shows a front panel of a control unit for use with the pliers of FIGS. 7 and 8.

The supply conductors 61 for the heating wire 53 are connected to respective sockets 71 on the control panel of the control unit 70, which is shown in FIG. 9. Likewise, the thermistor conductors 65 are connected to a corresponding socket 72 on the control unit 70. The control unit 70 has a ten position thumbwheel switch 73, by which a desired heat setting may be selected. A further switch unit 74 comprises a pair of Binary Coded Decimal (BCD) thumbwheel switches 75, by means of which a desired setting of a timer, between 0 and 99 seconds, may be selected.

Figure 10:
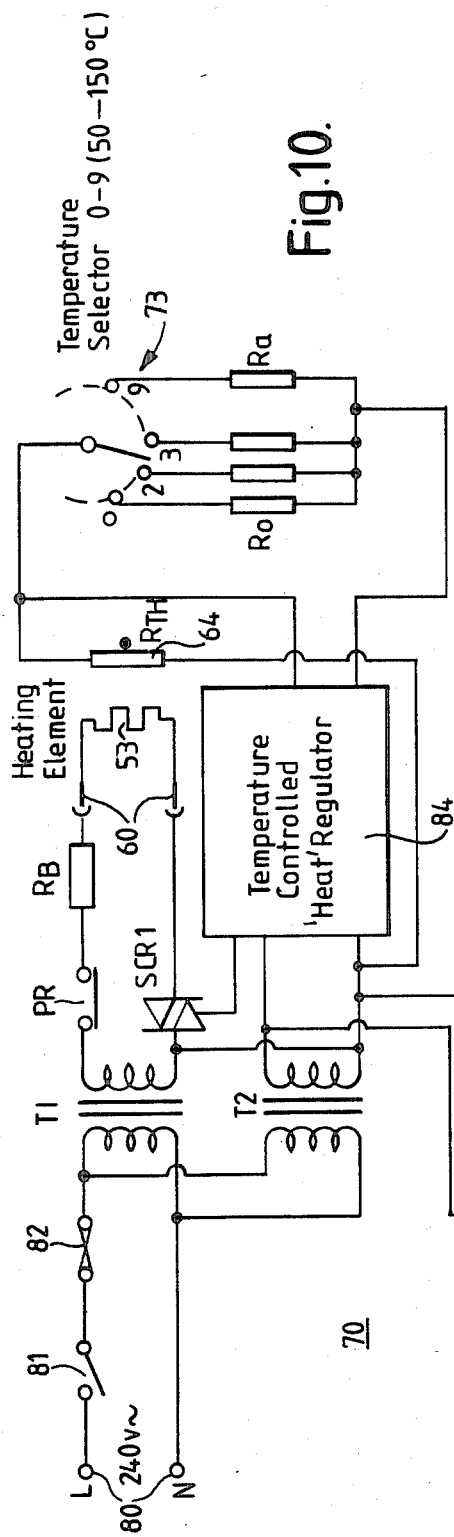
FIG. 10 is a circuit diagram of the control unit.
Figure 10:
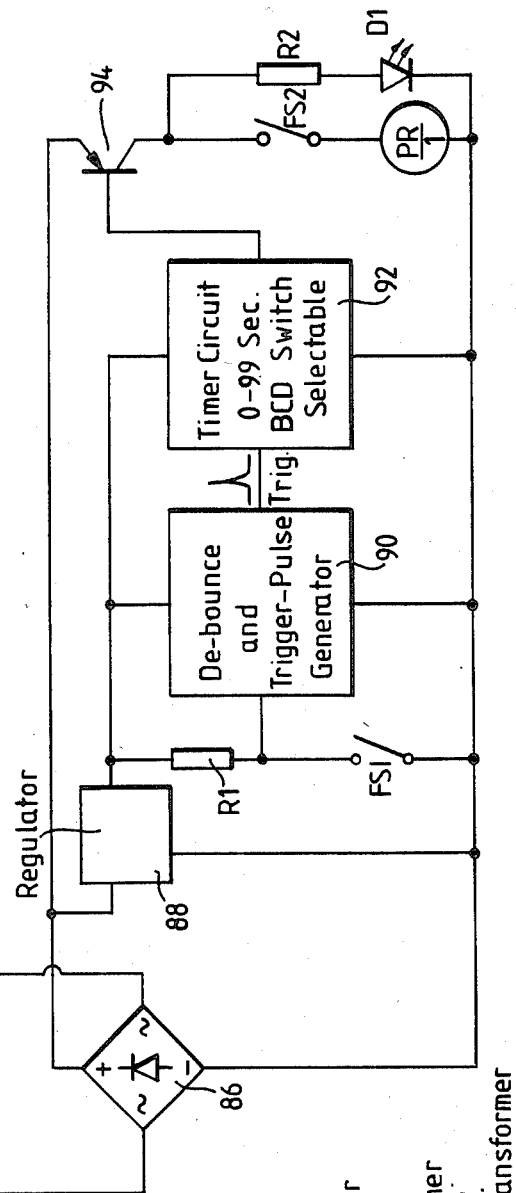

The circuitry of the control unit 70 is shown in more detail in FIG. 10.

A mains supply (e.g. 240 volts ac) is connected via a switch 81 and a fuse 82 to the primary side of a first transformer T1, and also to the primary side of a second transformer T2. To the secondary side of the first transformer T1 there is connected, in series, a Triac SCR1, a relay contact PR/1, a resistance RB, and the heating wire 53, via the terminal blocks 60.

The Triac SCR1 is controlled by a controller 84, which is connected to the secondary of the second transformer T2, and is also connected to receive control signals derived from the thermistor 64 and the heat-setting setting selector switch 73. It will be seen that the switch 73 contains a bank of ten resistors R0 to R9, each corresponding to a respective setting of the switch 73.

The secondary of the second transformer T2 is also fed to a bridge rectifier 86, the output of which is fed via a smoothing and regulating circuit 88 to a trigger pulse generator 90 and a timer circuit 92. The output of the regulator 88 is also adapted to be supplied to a control input of the trigger pulse generator 90, via a resistor R1. A switch contact FS1 is connected between the control input of the trigger pulse generator 90, and the negative side of the dc supply from the rectifier 86.

The output of the trigger pulse generator 90 is connected to the input of the timer circuit 92. The output of the timer circuit 92 is connected to the base of a switching transistor 94, in the collector leg of which there is connected, in series, a second switch contact FS2 and a relay PR/1. Connected in parallel with the switch FS2 and the relay PR/1 is a series combination of a resistor R2 and a light emitting diode D1.

The switch contacts FS1 and FS2 respond to an air-operated foot switch.

The illustrated pliers 40 and control unit 70 may be used as follows.

Firstly, the pliers 40 are applied to a nail to be treated, in a similar manner to the pliers 1. Thus, for example, the lower jaw 6 is disposed beneath the nail, with the forward, lower area 66 of the bottom jaw 6 in contact with the patient's toe, below the nail.

The desired heat-setting is selected by way of the switch 73, and the desired period of operation is selected by means of the switch 74.

The foot switch is then operated, and in response to the change in air pressure generated by such operation, the switch contacts FS1 and FS2, which are normally open, are closed.

Closure of the switch contact FS1 causes initiation of a trigger pulse from the generator 90, and the trigger pulse is fed to the timer circuit 92. The trigger pulse generator 90 is also operative to smooth out any effects of bouncing of the switch contact FS1.

Upon receiving the trigger pulse, the timer circuit 92 emits a low output, which causes the output transistor 94 to switch ON, thereby energising the really PR/1, via the second foot switch contact FS2. For as long as the output transistor 94 remains ON, the light emitting diode D1 glows.

When the relay PR/1 is energised, the respective contacts PR/1 are closed, to close the secondary circuit of the first transformer T1. Current is supplied to the heating wire 53, thereby causing the temperature of the nail to rise.

As mentioned above, the controller 84 regulates the supply of current to the heating wire 53, by means of the Triac SCR1. The thermistor 64 senses the temperature in the vicinity of the heating wire 53, and the controller 84 responds to the condition of the thermistor, to maintain the supply of current to the heating wire at such a level as to maintain the desired temperature. It will be appreciated that, in addition to providing the power supply for the rectifier bridge 86, the secondary of the second transformer T2 provides phase information to the controller 84. The Triac is fired in bursts, under the control of the controller 84. The voltage across the thermistor 64 is fed back to an error amplifier within the controller, the output of which amplifier is compared with a ramp, which is synchronised to the mains. Appropriate pulses are generated to fire the Triac in bursts. The error amplifier, comparator, ramp generator and pulse generator are all contained within a single integrated circuit.

After the predetermined time interval, the output of the timer circuit goes high, switching the output transistor OFF, and thereby deenergising the relay PR/1, and causing the light emitting diode D1 to go out.

It will be appreciated that, should it be necessary for the operator to reduce the heat input or remove power during a timed period, this may be achieved simply by releasing the foot switch, whereupon the relay PR/1 drops out. If the foot switch is reactivated during the timed period, then power will be re-applied until the original preset time interval is complete, or until the foot switch is released, if this precedes completion of the time interval. The foot switch may be released and reactivated a number of times during a time interval, if required. Once the present time interval has elapsed, the timer will reset, and subsequent foot switch operation will re-initiate the timing sequence.

The interlocking of the foot switch and the timer with the power relay provides a useful safety feature, in that power may always be instantly removed, at the operator's discretion. A further safety feature is that the foot switch comprises an air actuator, having no electrical wires outside the control unit 70. Moreover, the circuitry operates at low voltage, and is electrically isolated from the mains, via the transformers T1 and T2. By way of example, the transformers T1 and T2 may be arranged to provide outputs in the range 6 volts to 24 volts dc.

Although a thermistor 64 is used as a temperature sensor, alternative means may be employed such as, for example, a thermocouple or platinum resistance probe.

Although the invention has particular application to the treatment of nails, it may be adapted for use in the treatment of any horny thermoplastic which is grown by animals. For example, apparatus in accordance with the invention may be used in the clipping of hen beaks, in which case the instrument could incorporate appropriate cutting means.

In a variation of the pliers 1 and 40, the lower jaw 6 may additionally be provided with heating means, to heat the lower surface of a nail. However, the arrangement would have to be such as to ensure that the area of the lower jaw which may contact the body of the patient, other than the nail, is so arranged as to undergo no appreciable rise in temperature under any heating effect of the heating means.

In another variation, the bottom jaw 6 may be removable, or incorporate a removable portion, such that various different bottom jaw configurations may be selected, to afford bottom jaws of various sizes and/or having various gaps when the pliers are closed, to accommodate different nail thicknesses. The respective pliers may be slip-jointed, to afford different gaps between the jaws, when the pliers are closed. The bottom jaws may incorporate a spring loaded portion, so as to provide automatic compensation for different nail thicknesses.

We claim:

1. An instrument for treating a deformed nail having a nail bed on a human patient, said instrument comprising:
    a first jaw;
    a thermally insulating portion on said first jaw;
    an electrical heating element mounted on said thermally insulating portion, whereby heating is confined to the region of said heating element, said electrical heating element having a low thermal mass, such that it is operative to heat up and cool down rapidly;
    a second jaw cooperable with said first jaw;
    means for opening and closing said first and second jaws;
    said first and second jaws cooperating to clamp therebetween a portion of said nail, with said electrical heating element in direct thermal contact with a face of said nail, to thereby apply sufficient heat to said nail to facilitate bending thereof; and
    a thermal protection portion on one of said jaws, said thermal protection portion protecting said nail bed from temperatures prevailing at said electrical heating element, so that the patient is not subjected to discomfort by burning.

2. An instrument according to claim 1, wherein said thermal protection portion comprises a portion of thermally conducting material which has a high heat mass, to serve as a heat sink for heat generated by said electrical heating element.

3. An instrument according to claim 2, wherein said thermal protection portion is on said second jaw.

4. An instrument according to claim 1, wherein said thermal protection portion comprises a portion of thermally insulating material.

5. An instrument according to claim 4, wherein said thermal protection portion is on said first jaw.

6. An instrument according to claim 1, wherein said electrical heating element extends longitudinally of said first jaw, and said second jaw is formed with a corresponding longitudinal groove which is disposed below said element.

7. An instrument according to claim 1, wherein the instrument is in the form of pliers, said first and second jaws are pivotally connected together, and said pliers have handles which afford said opening and closing means and are connected to said jaws.

8. An instrument according to claim 1, wherein said jaws are substantially parallel when nearly closed but with a predetermined gap therebetween.

9. An instrument according to claim 1, wherein said first jaw has a convex surface to fit under a nail, said thermally insulating portion and said electrical heating element are provided on said convex surface, said thermal protection portion is provided on said first jaw, and said second jaw has a concave surface to cooperate with the convex surface of said first jaw.

10. An instrument according to claim 1, further comprising supply means arranged to supply a heating current to said electrical heating element to heat said element to a temperature in excess of 100 degrees Celsius.

11. An instrument according to claim 1, further comprising supply means arranged to supply a heating current to said electrical heating element to heat said element to a temperature of up to 150 degrees Celsius.

12. An instrument according to claim 1, further comprising control means arranged to supply a heating current to said electrical heating element and to limit said current to a predetermined value.

13. An instrument according to claim 12, wherein said control means includes temperature sensor means arranged to sense temperature in the vicinity of said electrical heating element, and said control means is arranged to control said current in response to an output of said sensor means.

14. An instrument according to claim 12, wherein said control means includes a timer arranged to allow said current to flow for a predetermined time.

15. An instrument according to claim 12, wherein said control means includes a timer arranged to allow said current to flow for a predetermined time, and indicator means arranged to indicate operation of the timer.

* * * * *